US008970380B2

United States Patent
Buco et al.

(10) Patent No.: US 8,970,380 B2
(45) Date of Patent: *Mar. 3, 2015

(54) SYSTEM AND METHOD FOR VERIFYING PATIENT COMPLIANCE

(71) Applicant: International Business Machines Corporation, Armonk, NY (US)

(72) Inventors: Melissa J. Buco, Bluffton, SC (US); David M. Loewenstern, New York, NY (US); Florian Pinel, New York, NY (US); Larisa Shwartz, Scarsdale, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/966,995

(22) Filed: Aug. 14, 2013

(65) Prior Publication Data

US 2014/0354433 A1    Dec. 4, 2014

Related U.S. Application Data

(63) Continuation of application No. 13/903,400, filed on May 28, 2013.

(51) Int. Cl.
   *G08B 13/14*   (2006.01)
   *G06Q 50/22*   (2012.01)
   *G06K 19/07*   (2006.01)

(52) U.S. Cl.
   CPC ............ *G06Q 50/22* (2013.01); *G06K 19/0723* (2013.01)
   USPC .................................... 340/572.4; 340/573.1

(58) Field of Classification Search
   USPC ............... 340/572.4, 573.1, 572.1; 206/459.1
   See application file for complete search history.

(56) References Cited

U.S. PATENT DOCUMENTS

| | | | |
|---|---|---|---|
| 6,294,999 | B1 | 9/2001 | Yarin et al. |
| 7,002,476 | B2 | 2/2006 | Rapchak |
| 7,253,734 | B2 | 8/2007 | Moskowitz |
| 7,382,263 | B2 | 6/2008 | Danowski et al. |
| 8,085,135 | B2 | 12/2011 | Cohen Alloro et al. |
| 2002/0067270 | A1* | 6/2002 | Yarin et al. .................. 340/573.1 |
| 2003/0007421 | A1* | 1/2003 | Niemiec et al. .................. 368/10 |
| 2010/0000899 | A1* | 1/2010 | Burg et al. .................. 206/459.1 |
| 2011/0163871 | A1 | 7/2011 | Einav et al. |
| 2011/0288380 | A1 | 11/2011 | Inciardi et al. |

(Continued)

OTHER PUBLICATIONS

P. Fuhrer et al., "Building a Smart Hospital Using RFID Technologies," in European Conference on eHealth (ECEH), Oct. 2006, pp. 131-142, vol. 91, Fribourg, Switzerland.

(Continued)

*Primary Examiner* — Shirley Lu
(74) *Attorney, Agent, or Firm* — Louis J. Percello; Ryan, Mason & Lewis, LLP

(57) ABSTRACT

A system for verifying compliance, comprises an input device including a radio-frequency identification (RFID) reader module, wherein the RFID reader module is capable of determining that an RFID tag corresponding to a medication dose in a product packaging is not detectable, and recording a time of the determination that the RFID tag is not detectable, a network, and a data management service module which is capable of receiving from the input device via the network information corresponding to the RFID tag and the time when the RFID tag was determined not detectable.

8 Claims, 3 Drawing Sheets

(56) References Cited

U.S. PATENT DOCUMENTS

2013/0232082 A1* 9/2013 Krawczewicz et al. ......... 705/55
2014/0262919 A1* 9/2014 Hussain et al. ............... 206/534

OTHER PUBLICATIONS

Dadong Wan, "Magic Medicine Cabinet: A Situated Portal for Consumer Healthcare," First International Symposium on Handheld and Ubiquitous Computing (HUC), Lecture Notes in Computer Science (LNCS), Sep. 1999, pp. 352-355, vol. 1707, Karlsruhe, Germany.

A. Dohr et al., "The Internet of Things for Ambient Assisted Living," IEEE Seventh International Conference on Information Technology: New Generations (ITNG), Apr. 2010, pp. 804-809.

F. Siegemund et al., "Interaction in Pervasive Computing Settings Using Bluetooth-Enabled Active Tags and Passive RFID Technology Together with Mobile Phones," First IEEE International Conference on Pervasive Computing and Communications (PerCom), Mar. 2003, pp. 378-387.

J.P. García-Vázquez et al., "Supporting the Strategies to Improve Elders' Medication Compliance by Providing Ambient Aids," Personal and Ubiquitous Computing, Apr. 2011, pp. 389-397, vol. 15, No. 4.

* cited by examiner

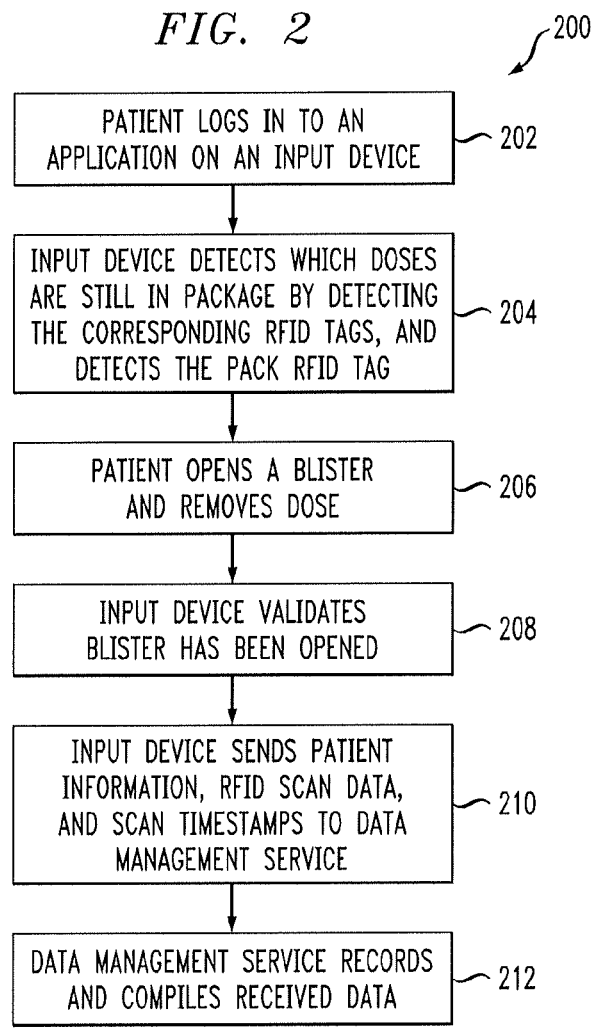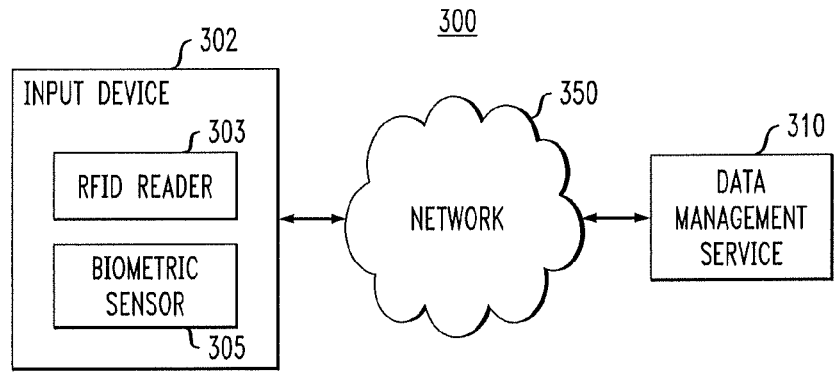

410

SYSTEM AND METHOD FOR VERIFYING PATIENT COMPLIANCE

CROSS-REFERENCE TO RELATED APPLICATION

This application is a Continuation of U.S. application Ser. No. 13/903,400, filed on May 28, 2013, the disclosure of which is incorporated herein in its entirety by reference.

TECHNICAL FIELD

The field generally relates to systems and methods for verifying patient compliance, and, in particular, to systems and methods for verifying patient drug compliance using radio-frequency identification (RFID).

BACKGROUND

Detection of non-compliance by patients when taking proscribed medication has become increasingly important, for example, in phase 3 testing (dosage determination) for FDA approval and follow-up testing. Further, in general, drug non-compliance can result in billions of dollars of costs to patients, drug manufacturers, insurance companies, hospitals, etc.

Drug non-compliance can occur, for example, when a patient (1) forgets to take the medication, (2) takes the wrong dosage, (3) takes the medication at the wrong time, and/or (4) exercises bad faith.

Systems and methods for detection of non-compliance can be useful if they support double-blind studies and patient anonymity, require little or no human monitoring or patient training, do not place a burden on the patient, and are inexpensive.

Accordingly, there exists a need for a solution which verifies patient compliance while preserving the features noted above.

SUMMARY

In general, exemplary embodiments of the invention include systems and methods for verifying patient compliance and, in particular, to systems and methods for verifying patient drug compliance using radio-frequency identification (RFID).

According to an exemplary embodiment of the present invention, a system for verifying patient compliance, comprises an input device including a radio-frequency identification (RFID) reader module, wherein the RFID reader module is capable of determining that an RFID tag corresponding to a medication dose in a product packaging is not detectable, and recording a time of the determination that the RFID tag is not detectable, a network, and a data management service module which is capable of receiving from the input device via the network information corresponding to the RFID tag and the time when the RFID tag was determined not detectable.

According to an exemplary embodiment of the present invention, a method for verifying patient compliance comprises corresponding a plurality of medication doses in a product packaging to respective radio-frequency identification (RFID) tags, determining that an RFID tag of the respective RFID tags is not detectable by an RFID reader, recording a time of the determination that the RFID tag is not detectable, and sending information corresponding to the RFID tag and the time when the RFID tag was determined not detectable to a data management service.

According to an exemplary embodiment of the present invention, a computer readable storage medium comprises program code tangibly embodied thereon, which when executed by a computer, performs method steps for verifying patient compliance, the method steps comprising corresponding a plurality of medication doses in a product packaging to respective radio-frequency identification (RFID) tags, determining that an RFID tag of the respective RFID tags is not detectable by an RFID reader, recording a time of the determination that the RFID tag is not detectable, and sending information corresponding to the RFID tag and the time when the RFID tag was determined not detectable to a data management service.

According to an exemplary embodiment of the present invention, a method for providing a user with data for verifying patient medication intake compliance, comprises corresponding a plurality of medication doses in a product packaging to respective radio-frequency identification (RFID) tags, determining that an RFID tag of the respective RFID tags is not detectable by an RFID reader, recording a time of the determination that the RFID tag is not detectable, repeating the determining and the recording steps for the plurality of medication doses over a designated period of time, generating a compliance report based on results of the recording and determining steps for the plurality of medication doses over the designated period of time, and providing the compliance report to the user in response to a request by the user.

These and other exemplary embodiments of the invention will be described or become apparent from the following detailed description of exemplary embodiments, which is to be read in connection with the accompanying drawings.

BRIEF DESCRIPTION OF THE DRAWINGS

Exemplary embodiments of the present invention will be described below in more detail, with reference to the accompanying drawings, of which:

FIG. 2 is a workflow diagram illustrating a method for verifying patient compliance according to an exemplary embodiment of the invention.

FIG. 3 is a high-level diagram of a system for verifying patient compliance, according to an embodiment of the present invention.

DETAILED DESCRIPTION OF EXEMPLARY EMBODIMENTS

Exemplary embodiments of the invention will now be discussed in further detail with regard to systems and methods for verifying patient drug compliance using radio-frequency identification (RFID). This invention may, however, be embodied in many different forms and should not be construed as limited to the embodiments set forth herein.

Embodiments of the present invention utilize RFID tags/chips applied to medication packaging in order to verify whether patients are correctly taking proscribed medications.

The methods of embodiments of the present invention require no expertise on the part of the patient and no human supervision of the patient, and are robust against accidental non-compliance and some types of deliberate non-compliance. Even in the case of deliberate and ongoing fraud by a patient, in accordance with embodiments of the present invention, a patient would be limited to removing single doses at a time.

In accordance with an embodiment of the present invention, an RFID tag includes an RF transmitter and receiver, and is interrogated by an encoded radio signal from an RFID reader. Upon receipt of the radio signal, the tag responds with the electronic identification information assigned to the tag, such as, for example, a unique tag serial number, product-related information, or other specific information. In accordance with embodiments of the present invention, RFID tags can include an integrated circuit for storing and processing information, for modulating and demodulating RF signals, for collecting DC power from an incident reader signal, and for other specialized functions; and an antenna for receiving and transmitting the signals.

In accordance with embodiments of the present invention, each dose has a unique ID, which is appropriate for protocols involving multiple medications and/or changing dosages. Embodiments of the present invention are applicable to double-blind studies, provide an accurate record of the time when each individual dose was taken, and do not interfere with the manufacture of the medications since the RFID tags and components are applied to the packaging, and not the drugs themselves. RFID attachments to packaging are inexpensive (e.g., bulk RFID tags may cost $0.15 per tag) and harmless, do not compromise the medication, and are resistant to tampering.

Figure 1A:
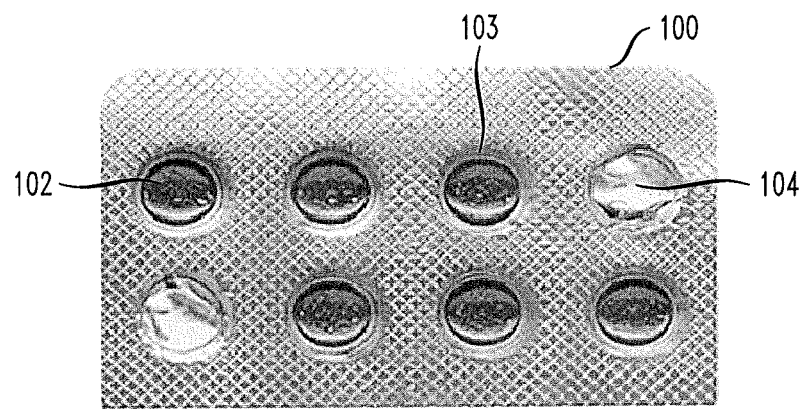
FIGS. 1A and 1B are diagrams illustrating respective front and back sides of medication packaging equipped with RFID tags in accordance with an embodiment of the present invention.
Figure 1B:
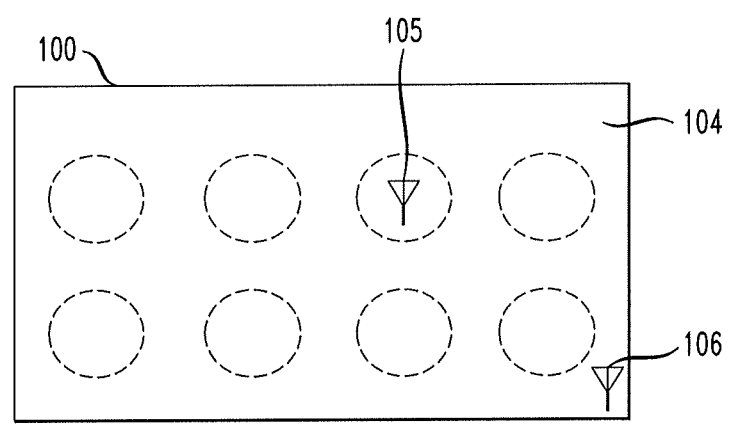

Referring to FIGS. 1A and 1B, which are diagrams illustrating respective front and back sides of medication packaging equipped with RFID tags in accordance with an embodiment of the present invention, the packaging is, for example, a blister pack 100, in which doses 102 are individually packaged in respective blisters 103. The backing 104 can be ripped or broken relatively easily using, for example, pressure and/or a relatively sharp object, such as a fingernail. In addition, in accordance with an embodiment, the backing is a non-conductor capable of accommodating electrical components. In an embodiment, the backing 104 is printed with the antennas for receiving and transmitting the signals, which use, for example, conductive ink to function. One blister antenna 105 is printed on the backing 104 at each respective blister 103. Breaking of the backing for a particular blister 103 also breaks the antenna 105. A pack antenna 106 is printed on a part of the backing 104 that does not cover a blister 103.

Each antenna 105, 106 is associated with a RFID tag, which can be, for example, layered within the blister pack 100 or stored separately and attachable to the blister pack, with, for example, a clip. Accordingly, each blister 103 has a unique blister antenna 105, RFID tag, and identifying information that is transferable by the RFID tag via the unique blister antenna 105. The pack itself has its own unique pack antenna 106, RFID tag, and identifying information that is transferable by the RFID tag via the unique pack antenna 106.

Referring to FIG. 2, which is a workflow diagram illustrating a method 200 for verifying patient compliance according to an exemplary embodiment of the invention, a patient logs in to, for example, an application on an input device (Block 202). The input device can be, for example, a smart phone or other portable electronic device, such as, for example, a notebook computer, tablet or personal digital assistant (PDA) capable of connecting to the Internet or other network, including, but not limited to, a local area network (LAN) or a wide area network (WAN). The input device is also not limited to a portable device, and may include, but is not limited to, a personal computer. In accordance with embodiments of the present invention, the patient may log in to an application, such as a mobile application, using a user ID and password. In an embodiment, the input device can be capable of identifying a user (such as through biometrics) using, for example, fingerprint matching. The input device is also equipped with an RFID reader.

At block 204, the input device detects which doses remain in the package by detecting the corresponding RFID tags, and also detects the pack RFID tag. The patient/user may facilitate detection of the RFID tags by scanning the package with the input device including the RFID reader. According to an embodiment, block 204 is optional, and may be omitted.

At block 206, the patient opens a blister and removes dose. Opening a blister breaks the blister antenna for that dose. At block 208, the input device validates that a blister has been opened because the RFID tag corresponding to that blister is not detected, and the RFID tag for the pack is still detected.

At block 210, the input device sends patient information (e.g., identity, identification number, etc.), RFID scan data (e.g., the unique identification information associated with detected tags, and information regarding which tags are no longer detected), and scan timestamps (e.g., to determine when connections were severed) to a data management service via the network. According to an embodiment, the data management service is available via the Internet.

At block 212, the data management service records and compiles the received data, which can be audited by a user, such as a pharmaceutical company, physicians, nurses, other medical professionals, etc. According to embodiments, the data management service can be responsible for receiving the drug use data from the input devices, managing inferences of missed or incorrectly administered doses from the data, and providing reports on patient compliance as requested by auditors. The data management service can maintain confidentiality and anonymity through different levels of security for auditors, input devices, and other personnel.

According to an exemplary embodiment of the present invention, over the course of a compliance period (e.g., a predetermined time period for a medication study, or for taking a prescribed medication), a data management service can provide subscribers with data (e.g., in the form of compliance reports) for verifying medication intake compliance of patients. The data management service can, over the compliance period, compile determinations of when respective RFID tags for each of a plurality of medication doses were no longer detectable by an RFID reader, and generate a compliance report based on results of the determinations. The compliance report may, for example, include conclusions of whether patients consumed the proper amounts of medication and the proper time based on comparisons to an expected intake schedule or plan. The data management service can provide the compliance report to the subscriber, such as a medical or pharmaceutical professional, in response to a request by the subscriber for such a report. The data management service can be, for example, a web-based service capable of collecting medication use data and receiving requests for information from a variety of input devices, such as, for example, smart phones and tablets.

Referring to FIG. 3, which is a high-level diagram of a system for verifying patient compliance, according to an embodiment of the present invention, the system 300 includes an input device 302 having an RFID reader module 303 and at least one biometric sensor module 305, a data management service module 310 and a network 350 to which the input device 302 and the data management service module 310 are connected. As noted above, the input device 302 can be, for example, a smart phone or other electronic device capable of connecting to the network 350, which can be, for example, the Internet or other network, including, but not limited to, a LAN or WAN. In accordance with embodiments of the present invention, the patient may log in to an application, such as a mobile application, via the input device 302. In an embodiment, the input device 302, which includes one or more processors, is capable of identifying and logging in a user using the biometric sensor module 305. The biometric sensor module 305 includes one or more biometric sensors for sensing biometric traits of a user, such as, for example, fingerprints. With the aid of a processor, the biometric sensor module 305 matches the sensed traits with user profile information in a database.

The input device 302 is also equipped with an RFID reader module 303, which includes an RFID reader and enables the input device 302 to detect RFID tags corresponding to remaining medication doses in a package, and the RFID tag corresponding to the packaging. The patient/user may facilitate detection of the RFID tags by scanning the package with the input device 302.

With the aid of a processor, the RFID reader module 303 validates that a blister has been opened when the reader module 303 determines that an RFID tag corresponding to an open blister is no longer detected, and the RFID tag for the pack is still detected. For example, according to an embodiment, the RFID reader module 303 detects the RFID tags and stores (e.g., in a database) the unique identification information for the respective blisters prior to opening of the blisters. Upon opening of a blister, and breaking of the antenna, the RFID reader module 303 is able to determine that an RFID tag for the broken blister is no longer detected. According to an embodiment, the RFID reader module 303 records the time when the RFID tag for the broken blister was no longer detected for an eventual conclusion of when the medication was removed from the packaging and administered. In accordance with embodiments of the present invention, when activated, the RFID reader module 303 can continuously or periodically (e.g., every 30 seconds, 2 minutes, etc.) scan for the presence of RFID tags.

The input device 302 sends patient information, RFID scan data, and scan timestamps to the data management service module 310 via the network 350. The data management service module 310 includes the necessary hardware and software components for the data management service module 310 to at least record and compile the received data, which can be audited by a user accessing the data management service module 310 via the network 350. According to embodiments, the data management service module 310 receives the drug use data from the input devices, manages inferences of missed or incorrectly administered doses from the data, and provides reports on patient compliance as requested by auditors.

As will be appreciated by one skilled in the art, aspects of the present invention may be embodied as a system, apparatus, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

FIGS. 1-3 illustrate the architecture, functionality, and operation of possible implementations of systems, methods, and computer program products according to various embodiments of the present invention. In this regard, each block in a flowchart or a block diagram may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagram and/or flowchart illustration, and combinations of blocks in the block diagram and/or flowchart illustration, can be implemented by special purpose hardware-based systems that perform the specified functions or acts, or combinations of special purpose hardware and computer instructions.

Figure 4:
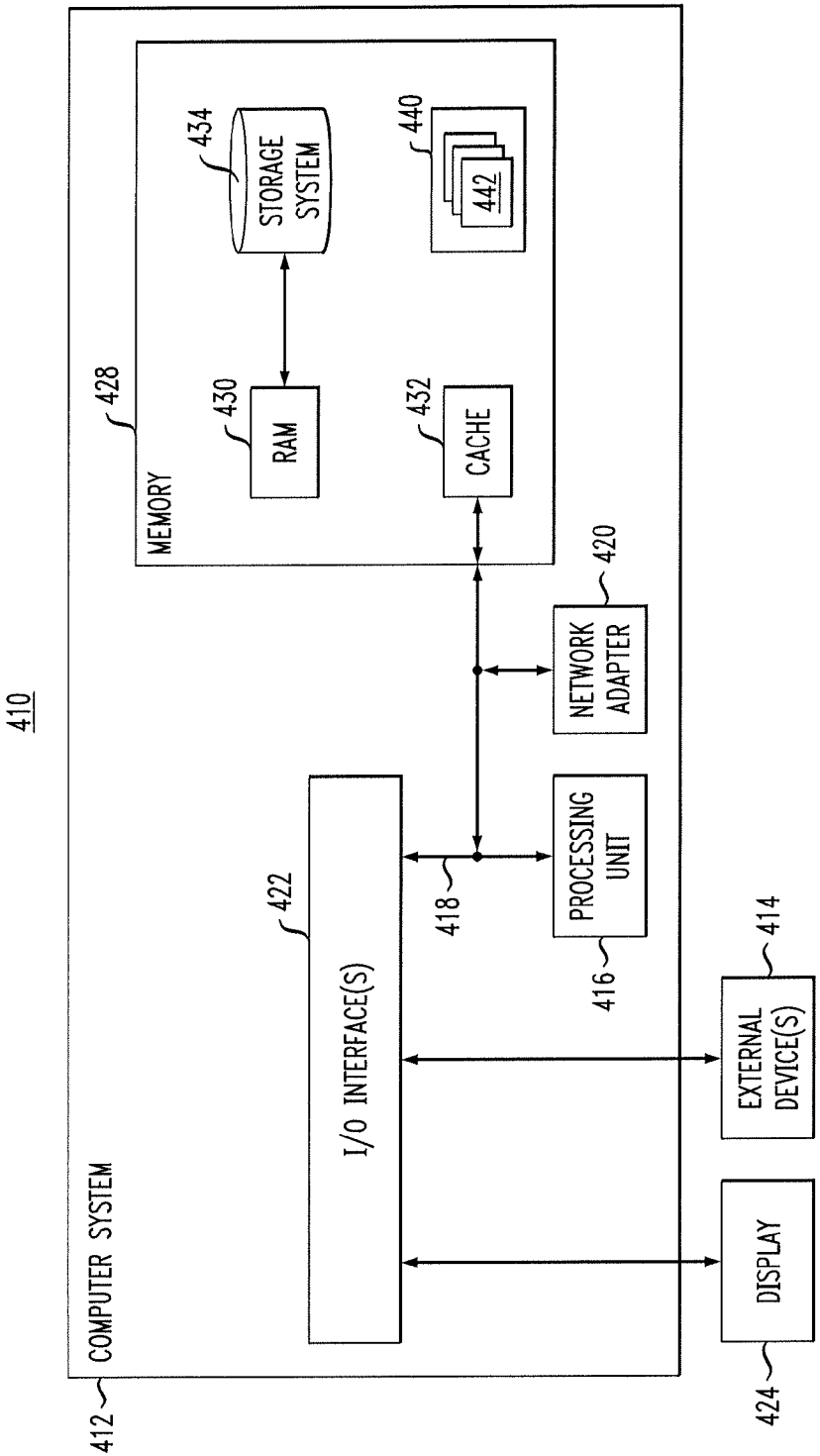
FIG. 4 illustrates a computer system in accordance with which one or more components/steps of the techniques of the invention may be implemented, according to an exemplary embodiment of the invention.

One or more embodiments can make use of software running on a general-purpose computer or workstation. With reference to FIG. 4, in a computing node 410 there is a computer system/server 412, which is operational with numerous other general purpose or special purpose computing system environments or configurations. Examples of well-known computing systems, environments, and/or configurations that may be suitable for use with computer system/server 412 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 412 may be described in the general context of computer system executable instructions, such as program modules, being executed by a computer system. Generally, program modules may include routines, programs, objects, components, logic, data structures, and so on that perform particular tasks or implement particular abstract data types. Computer system/server 412 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 4, computer system/server 412 in computing node 410 is shown in the form of a general-purpose computing device. The components of computer system/server 412 may include, but are not limited to, one or more processors or processing units 416, a system memory 428, and a bus 418 that couples various system components including system memory 428 to processor 416.

The bus 418 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The computer system/server 412 typically includes a variety of computer system readable media. Such media may be any available media that is accessible by computer system/server 412, and it includes both volatile and non-volatile media, removable and non-removable media.

The system memory 428 can include computer system readable media in the form of volatile memory, such as random access memory (RAM) 430 and/or cache memory 432. The computer system/server 412 may further include other removable/non-removable, volatile/nonvolatile computer system storage media. By way of example only, storage system 434 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 418 by one or more data media interfaces. As depicted and described herein, the memory 428 may include at least one program product having a set (e.g., at least one) of program modules that are configured to carry out the functions of embodiments of the invention. A program/utility 440, having a set (at least one) of program modules 442, may be stored in memory 428 by way of example, and not limitation, as well as an operating system, one or more application programs, other program modules, and program data. Each of the operating system, one or more application programs, other program modules, and program data or some combination thereof, may include an implementation of a networking environment. Program modules 442 generally carry out the functions and/or methodologies of embodiments of the invention as described herein.

Computer system/server 412 may also communicate with one or more external devices 414 such as a keyboard, a pointing device, a display 424, etc., one or more devices that enable a user to interact with computer system/server 412, and/or any devices (e.g., network card, modem, etc.) that enable computer system/server 412 to communicate with one or more other computing devices. Such communication can occur via Input/Output (I/O) interfaces 422. Still yet, computer system/server 412 can communicate with one or more networks such as a local area network (LAN), a general wide area network (WAN), and/or a public network (e.g., the Internet) via network adapter 420. As depicted, network adapter 420 communicates with the other components of computer system/server 412 via bus 418. It should be understood that although not shown, other hardware and/or software components could be used in conjunction with computer system/server 412. Examples, include, but are not limited to: microcode, device drivers, redundant processing units, external disk drive arrays, RAID systems, tape drives, and data archival storage systems, etc.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

We claim:

1. A system for verifying compliance, comprising:
 an input device including a radio-frequency identification (RFID) reader module, wherein the RFID reader module is capable of determining that an RFID tag corresponding to a medication dose in a product packaging is not detectable, and recording a time of the determination that the RFID tag is not detectable, wherein the RFID tag is one of a plurality of RFID tags in the product packaging, each respective RFID tag corresponding to a medication dose of a plurality of medication doses in the product packaging, and including an integrated circuit and an antenna located on a portion of the product packaging that must be broken in order for a user to access a corresponding medication dose;
 a network; and
 a data management service module which is capable of receiving from the input device via the network information corresponding to the RFID tag and the time when the RFID tag was determined not detectable;
 wherein the RFID tag is rendered not detectable when the user, by breaking the portion of the product packaging to access the corresponding medication dose, also breaks the antenna of the corresponding RFID tag;
 wherein the RFID reader module is further capable of detecting an RFID tag corresponding to the product packaging, wherein the RFID tag corresponding to the product packaging remains detectable when the respective RFID tags are not detectable, and is located on a portion of the product packaging that remains intact when the user accesses each of the plurality of medication doses.

2. The system according to claim 1, wherein the input device includes a biometric sensor module capable of identifying and logging in a user using a biometric trait of the user.

3. The system according to claim 1, wherein the RFID reader module is capable of detecting the respective RFID tags corresponding to the plurality of medication doses in the product packaging.

4. The system according to claim 1, wherein the antenna includes conductive ink.

5. The system according to claim 1, wherein the data management service is capable of generating a compliance report based on the time when the RFID tag was determined not detectable.

6. The system according to claim 1, wherein the input device comprises a portable electronic device capable of connecting to the network.

7. The system according to claim 1, wherein the integrated circuit for each respective RFID tag stores and processes information, modulates and demodulates RF signals, and collects DC power from an incident reader signal.

8. A computer readable storage medium comprising program code tangibly embodied thereon, which when executed by a computer, performs method steps for verifying compliance, the method steps comprising:
 corresponding a plurality of medication doses in a product packaging to respective radio-frequency identification (RFID) tags, each respective RFID tag including an integrated circuit and an antenna located on a portion of the product packaging that must be broken in order for a user to access a corresponding medication dose;
 determining that an RFID tag of the respective RFID tags is not detectable by an RFID reader;
 recording a time of the determination that the RFID tag is not detectable; and
 sending information corresponding to the RFID tag and the time when the RFID tag was determined not detectable to a data management service;
 wherein the RFID tag is rendered not detectable when the user, by breaking the portion of the product packaging to access the corresponding medication dose, also breaks the antenna of the corresponding RFID tag;
 wherein the method steps further comprise corresponding an RFID tag to the product packaging, wherein the RFID tag corresponding to the product packaging remains detectable when the respective RFID tags are not detectable, and is located on a portion of the product packaging that remains intact when the user accesses each of the plurality of medication doses.

* * * * *